United States Patent [19]

Giordani et al.

[11] Patent Number: 4,879,300
[45] Date of Patent: Nov. 7, 1989

[54] NOVEL PIPERIDINE DERIVATIVES

[75] Inventors: Antonio Giordani; Vittorio Vecchietti, both of Milan, Italy

[73] Assignee: Dr. Lo. Zambeletti S.p.A., Italy

[21] Appl. No.: 135,839

[22] Filed: Dec. 21, 1987

[30] Foreign Application Priority Data

Dec. 22, 1986 [GB] United Kingdom ............. 8630639
Aug. 29, 1987 [GB] United Kingdom ............. 8720492

[51] Int. Cl.$^4$ .................. A61K 31/445; C07D 401/06
[52] U.S. Cl. ................................. 514/317; 514/326; 514/331; 546/189; 546/208; 546/226; 546/237
[58] Field of Search ............... 546/189, 208, 226, 237; 514/317, 326, 331

[56] References Cited

U.S. PATENT DOCUMENTS 2,684,965  7/1954  Weston et al. ............... 546/189
4,801,585  1/1989  Vecchietti et al. ........... 514/210

FOREIGN PATENT DOCUMENTS 1250719  10/1971  United Kingdom ........... 546/189

Primary Examiner—Robert T. Bond
Attorney, Agent, or Firm—Jacobs & Jacobs

[57] ABSTRACT

A compound, or a solvate or salt thereof, of formula I:

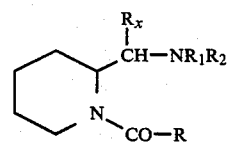

in which:

R.CO— is an acyl group containing a substituted or unsubstituted carbocyclic aromatic or heterocyclic aromatic group;

$R_1$ and $R_2$ are independently hydrogen, $C_{1-6}$ alkyl, $C_{1-6}$ alkenyl, $C_{1-6}$ cycloalkyl or $C_{1-12}$ cycloalkylalkyl or together form a $C_{2-6}$ polymethylene or $C_{2-6}$ alkenylene group, optionally substituted with a hetero-atom, provided that $R_1$ and $R_2$ are not simultaneously hydrogen;

Rx is $C_{1-6}$ alkyl or phenyl, or Rx together with $R_1$ form a —(CH$_2$)$_3$— or —(CH$_2$)$_4$— group, is useful for the treatment of pain.

19 Claims, No Drawings

NOVEL PIPERIDINE DERIVATIVES

This invention is concerned with novel piperidine derivatives, processes for their preparation, and their use in medicine, particularly as analgesics.

Compounds which are K-receptor agonists act as analgesics through interaction with Kappa opioid receptors. The advantage of K-receptor agonists over the classical μ-receptor agonists, such as morphine, lies in their ability to cause analgesia while being devoid of morphine-like behavioural effects and addiction liability.

European Published Application No. 232,612 discloses a group of piperidine derivatives which exhibit K-receptor agonism without the behavioural effects of morphine and morphine analogues, and which are thus of potential therapeutic utility as analgesics.

A novel class of structurally related piperidine derivatives has now been discovered which also exhibit potent K-receptor agonism without the aforementioned undesirable behavioural effects.

According to the present invention there is provided a compound, or a solvate or salt thereof, of formula I;

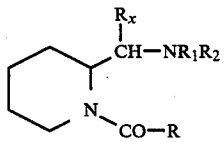
I in which: R.CO— is an acyl group containing a substituted or unsubstituted carbocyclic aromatic or heterocyclic aromatic group;

$R_1$ and $R_2$ are independently hydrogen, $C_{1-6}$ alkyl, $C_{2-6}$ alkenyl, $C_{2-6}$ cycloalkyl or $C_{4-12}$ cycloalkylalkyl groups or together form a $C_{2-6}$ polymethylene or $C_{2-6}$ alkenylene group, optionally substituted with a heteroatom, provided that $R_1$ and $R_2$ are not simultaneously hydrogen;

$R_x$ is $C_{1-6}$ alkyl preferably methyl or ethyl, or phenyl, or $R_x$ together with $R_1$ form a —(CH$_2$)$_3$— or —(CH$_2$)$_4$— group.

When used herein, the term 'carbocyclic aromatic group' includes single or fused rings, having 6 to 12 carbon atoms, and the term 'heterocyclic aromatic group' includes single or fused rings having 5 to 12 atoms, comprising up to four hetero-atoms in the or each ring, selected from oxygen, nitrogen and sulphur.

When the carbocyclic or heterocyclic group is a fused two ring system, one or both single rings may be aromatic in character. Suitably, one of the rings is aromatic and the other is non-aromatic.

When $R_1$ and $R_2$ are $C_{1-6}$ alkyl groups, examples are methyl, ethyl, propyl, butyl, pentyl or hexyl groups, preferably methyl.

Examples of $C_{2-6}$ alkenyl groups are 1- and 2- propenyl; an example of a $C_{3-6}$ cycloalkyl group is cyclopropyl, and an example of a $C_{4-12}$ cycloalkylalkyl group is cyclopropylmethyl.

When $R_1$ and $R_2$ together form a polymethylene group, examples are propylene, butylene, pentylene or hexylene, preferably butylene. As an alkenylene group, $R_1$-$R_2$ may be typically —CH$_2$—CH=CH—CH$_2$—. Examples of hetero-atoms are oxygen and sulphur, particularly oxygen, and a suitable hetero-atom substituted polymethylene group is —CH$_2$CH$_2$OCH$_2$CH$_2$—.

The group R preferably has the formula (II)

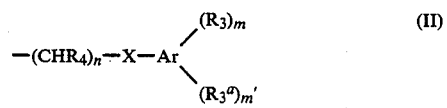
(II)

in which
n is 0, 1 or 2,
m is 0, 1 or 2,
M' is 0, 1 or 2, provided m+m'≦2;
X is a direct bond, or O, S or NR$_5$ in which R$_5$ is hydrogen or $C_{1-6}$ alkyl;
Ar is a substituted or unsubstituted carbocyclic aromatic or heterocyclic aromatic group,
each of $R_3$ and $R_3{}^a$ is an electron withdrawing substituent, $C_{1-6}$ alkoxy, $C_{1-6}$ haloalkoxy, $C_{1-6}$ alkyl, $C_{1-6}$ haloalkyl, $C_{2-6}$ haloalkenyl, $C_{2-6}$ haloalkynyl aryl or halogen or, when m is 2, and m' is 0 two $R_3$'s form a $C_{3-6}$ polymethylene group;
and $R_4$ is hydrogen or $C_{1-6}$ alkyl.

Examples of $R_3$ or $R_3{}^a$ are —NO$_2$, —CN, —CF$_3$, —Cl, Br,—OCF$_3$, —OCHF$_2$, —OCF$_2$CF$_2$H, —PCCl$_2$CF$_3$, —COOR$_6$, —CONR$_7$R$_8$, —SO$_3$R$_9$, —SO$_2$NR$_{11}$ or —COR$_{12}$ in which each of R$_6$ to R$_{12}$ is independently hydrogen, $C_{1-6}$ alkyl, aryl or aralkyl. When two $R_3{}^{,2}$ are linked they may form a fused cyclopentyl or cyclohexyl ring.

Examples of $R_4$ are methyl and ethyl, and preferably $R_4$ is hydrogen.

Preferably Ar is phenyl and $R_3$ or $R_3{}^a$ is preferably in the meta- and/or para- position.

Preferably, $R_3$ or $R_3{}^a$ is bromine, chlorine, —NO$_2$ or —CF$_3$, particularly in the meta- or para-position.

X is typically oxygen or a direct bond, and n is typically 0 or 1.

Examples of R are:

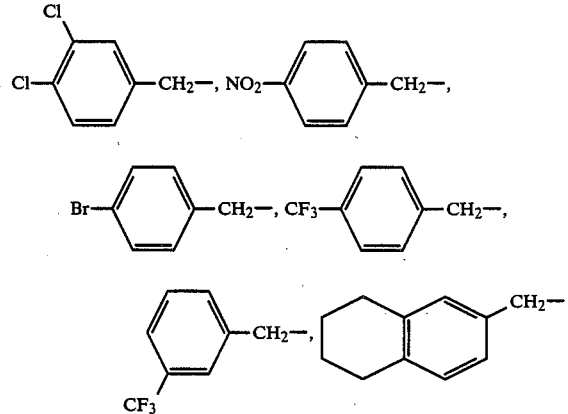

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least two asymmetric centres and therefore exist in more than one stereoisomeric form. The invention extends to all such forms and to mixtures thereof, including racemates.

The present invention also provides a process for the preparation of a compound of formula I which comprises reacting a compound of formula (III)

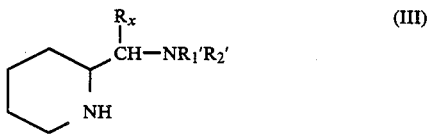

in which $R_1'$ and $R_2'$ are $R_1$ and $R_2$ as defined for formula (I) or a group or atom convertible to $R_1$ and $R_2$, and Rx is as defined for formula (I) with a compound of formula

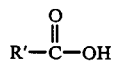

or an active derivative thereof, in which R' is R as defined for formula (I) or a group convertible to R, to form a compound of formula (Ia)

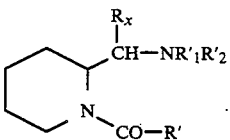

and then performing one or more of the following steps:

(a) where R', $R_1'$ $R_2'$ are other than R, $R_1$ and $R_2$, converting R', $R_1'$ or $R_{2l'}$ to R, $R_1$ or $R_2$ to obtain a compound of formula (I), (b) where R', $R_1'$ and $R_2'$ are R, $R_1$ and $R_2$, converting one R, $R_1$ or $R_2$ to another R, $R_1$ or $R_2$ to obtain a compound of formula (I), (c) forming a salt and/or solvate of the obtained compound of formula (I).

Suitable active derivatives of

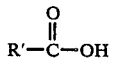

are acid chlorides or acid anhydrides. Another suitable derivative is mixed anhydride formed between the acid and an alkyl chloroformate.

For Example, in standard methods well known to those skilled in the art, the compound of formula (III) may be coupled:

(a) with an acid chloride in the presence of an inorganic or organic base, (b) with the acid in the presence of dicyclohexyl carbodiimide, N-dimethylaminopropyl-N'-ethyl carbodiimide or carbonyl diimidazole, (c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention. $R_1'$ and $R_2'$ may be alkyl groups and converted to $R_1'/R_2'$ hydrogen atoms by conventional amine dealkylation. When $R_1'$ or $R_2'$ is benzyl or substituted benzyl it may be converted to an $R_1$ or $R_2'$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process will generally provide a diastereoisomeric mixture which can subsequently separated into isomers by column chromatography.

The compound

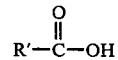

is typically of the formula (IIa)

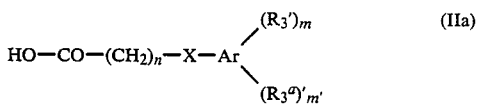

in which $R_3'$ is $R_3$ and $(R_3^1)'$ is $R_3^a$ as defined for formula (II) or a group or atom convertible to $R_3$ or $R_3^a$, the other variables being as defined for formula (II).

Conversions of substituents $R_3'$ or $R_3^{a'}$ on the aromatic group Ar to obtain $R_3$ or $R_3^a$ are generally known in the art of aromatic chemistry. $R_3'$ is preferably $R_3$, and $R_3^{a'}$ is preferably $R_3^a$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

The compound of formula (II) may be prepared from a compound of formula (IV) by the reaction scheme shown:

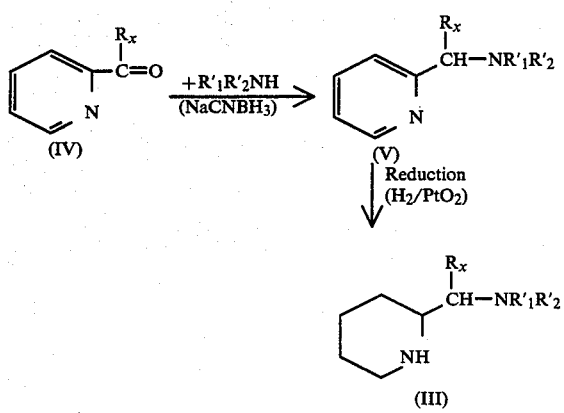

In this scheme, a compound of formula (IV) is treated with a secondary amine R₁R'₂NH in the presence of a reducing hydride, such as Na CNBH₃, to form a compound of formula (V). The latter is then reduced catalytically using hydrogen/PtO₂ to form a compound of formula (III).

The compound of formula (III) may also be prepared from a compound of formula (IV) by the following reaction scheme:

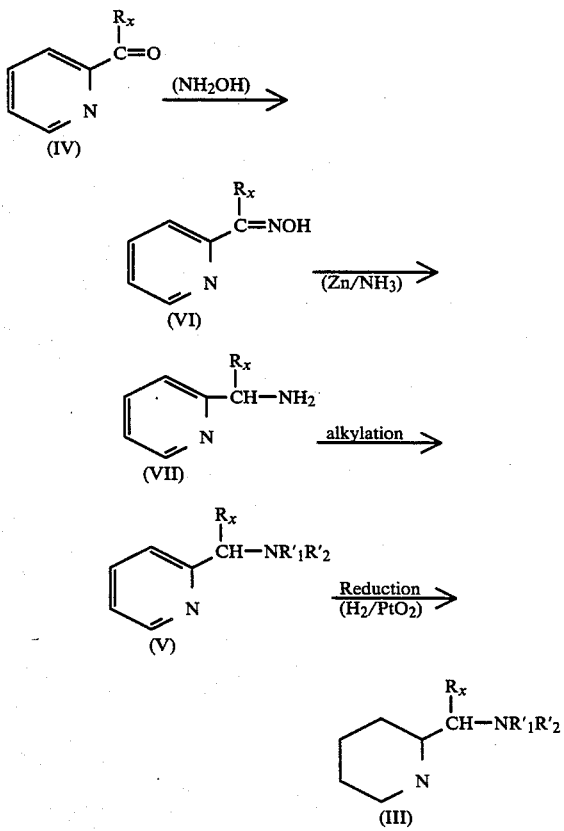

In this scheme, a compound of formula (IV) is transformed into an oxime of formula (VI) by treatment with hydroxylamine, which is then reduced to the corresponding amine of formula (VII) by, for example, treatment with zinc powder in ethanolic ammonia.

When each of R'₁ and R'₂ is an alkyl group, the compound of formula (VII) may be transformed to the amine of formula (V) by standard alkylation methods, such as, for example, the Leuckart-Wallach reaction (using HCHO and HCOOH) or by reaction with formaldehyde and NaCNBH₃.

When R'₁ and R'₂ together form a typical $C_{3-6}$ polymethylene group, namely butylene, a preferred transformation of a compound of formula (VII) to formula (Va) is achieved by treating the compound of formula (VII) with 4-chlorobutyroylchloride in the presence of an organic or inorganic base, cyclising the obtained amide of formula (VIII) by means of NaH, and reducing the obtained cyclic amide of formula (IX) using LiAlH₄, according to the following reaction scheme:

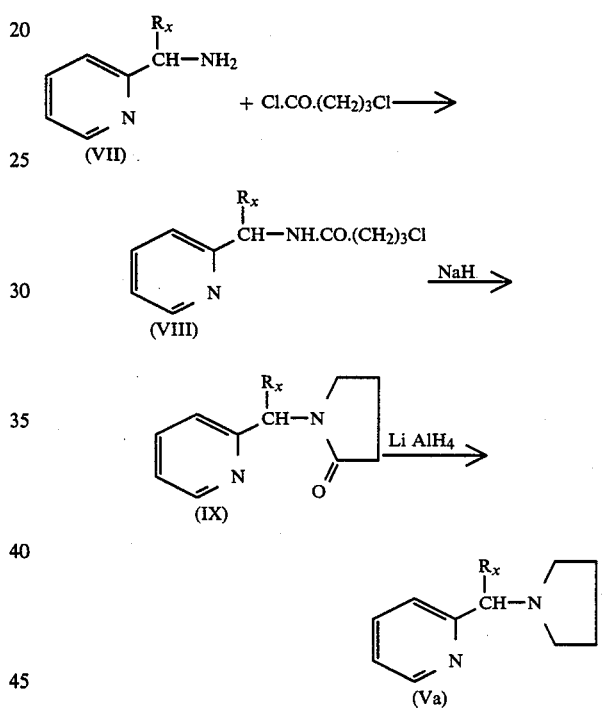

The compounds of formula (IV) are either known compounds or can be made from known compounds by known methods.

Compounds of formula (V) in which Rx and R₁' together form a —(CH₂)₃— or —(CH₂)₄— group are known [L. C. Craig, J.Am. Chem. Soc., 56 1144 (1934); Ramon Weil et al., Bull. Soc. Chim. France, 1974, 258] and these may be reduced to the corresponding compounds of formula (III) by known methods (Zh., Org. Khim. 1971, 7 (10, 2198–2201).

Certain of the intermediates described above are novel compounds and, together with the described processes for their preparation, they form a further aspect of this invention.

The activity of the compounds of formula (I) in standard analgesic tests indicates that they are of therapeutic utility in the treatment of pain.

Accordingly the present invention also provides a compound of formula (I), or a pharmaceutically acceptable salt or solvate thereof, for use as an active therapeutic substance, particularly for use in treating pain.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method of treating pain in mammals, particularly in humans, which comprises administering an effective amount of a compound of formula (I), or pharmaceutically acceptable salt or solvate thereof, to a sufferer.

Compounds of this invention and their preparation are illustrated in the following Examples. In the Examples, the diastereoisomers are separated by column chromatography and labelled isomer A and isomer B in order of increasing polarity.

EXAMPLE No 1

(A) 2-[1-(1-pyrrolidinyl)ethyl]pyridine

Ml 11.2 (0.1 moles) of 2-acetylpyridine (commercial product) and ml.16.5 (0.2 moles) of pyrrolidine were dissolved in ml.120 of dry methanol, and the solution was brought to pH 8 by adding HCl dissolved in methanol. Gr.9.4 (0.15 moles) of NaCNBH3 were added in small portions and the reaction mixture stirred 48 hours at room temperature. The mixture was brought to strongly basic pH by adding aqueous 20% NaOH, a small amount of insoluble filtered off, and the filtrate concentrated to small volume i.v. The residue was taken up in ether, the phases separated, and the aqueous layer extracted with ether. The combined ether solutions were washed with 20% aqueous Na OH, saturated aqueous NaCl and finally dried on NaOH pellets and evaporated to dryness i.v. 23 g. of red oil were obtained, and were chromatographed on 120 g. of silicagel, eluting with CH2Cl2 containing increasing amounts of metanol (0.5% to 8%). Gr 16 of oily product were obtained, sufficiently pure for the subsequent step.

(B)

[2-1-(1-pyrrolidinyl)ethyl]piperidine(diastereoisomeric mixture)

Gr 4 of 2- 1-(1-pyrrolidinyl)ethyl pyridine were dissolved in ml.50 CH3COOH, plus ml.2 of CF3COOH, and hydrogenated on 200 mg. of PtO2 at 60° C. and 3.5 atmospheres until the theoretical amount of hydrogen was consumed. The exhausted catalyst was filtered off and the filtrate evaporated in vacuo. The oil was taken up in 20% aqueous NaOH, the mixture repeatedly extracted with ether, the combined ethereal solutions dried and evaporated to dryness i.v. Gr 3.9 of oily product were obtained, sufficiently pure for the subsequent step.

(C)

1-(3,4-dichlorophenylacetyl)-2-[1-(1-pyrrolidinyl)ethyl]piperidine Diastereoisomer A Gr 5.2 (0.025 moles) of dicyclohexylcarbodiimide dissolved in ml.50 of CH2Cl2 were dropped into a solution of gr 3.9 (0.021 moles) of 2- 1-(1-pyrrolidinyl)ethyl piperidine and gr 4.5 (0.022 moles) of 3,4-dichlorophenylacetic acid in ml.80 of CH2Cl2, kept at 0° C. After 48 hours standing at room temperature, the precipitated diciclohexylurea was filtered off, and the filtrate was evaporated to dryness i.v. The oily residue was dissolved in ethyl acetate, and the solution extracted with 20% aqueous citric acid. The acidic solution was washed several times with ether and made alkaline by adding solid Na OH. The basic solution was repeatedly extracted with ether. The combined ether solutions were dried on Na2SO4 and evaporated to dryness i.v. The oily residue (mixture of diastereoisomers—gr 6) was chromatographed on 60 g. of silicagel, eluting with CH2Cl2 containing increasing amounts of methanol (0.2% to 1%). The fast moving diastereoisomer A was so obtained, and crystallized from methanol.

Yield g. 1.3
C19H26Cl2N2O
M.W. 369.33
M.P. 94°-6° C.

| NMR (CDCl3 - 80 MHz) | | | |
|---|---|---|---|
| delta = | 0.8 | d | 3H |
| | 1.0–1.9 | m | 10H |
| | 2.0–2.3 | m | 1H |
| | 2.4–2.7 | broad s | 4H |
| | 2.8–3.7 | m | 2H |
| | 3.7 | s | 2H |
| | 4.4–4.9 | m | 1H |
| | 7.0–7.55 | m | 3H |

EXAMPLE No 2

1-(3,4-dichlorophenylacetyl)-2-[1-(1-pyrrolidinyl)ethyl piperidine]—Diastereoisomer B After separating the isomer A, elution of the column was continued, using CH2Cl2 containing 1.2% to 8% of methanol and increasing amounts of ammonia (0.2% to 1%). After mixed fractions (diastereoisomer A+B), pure isomer B was collected, and crystallized from methanol.

Yield gr. 0.8
C19H26Cl2N2O
M.W. 369.33
M.P. 86°-7° C.

| NMR (CDCl3 - 80 MHz) | | | |
|---|---|---|---|
| delta = | 0.93 | d | 3H |
| | 1.3–1.8 | m | 10H |
| | 2.4–2.7 | m | 4H |
| | 3.0–3.55 | m | 3H |
| | 3.7 | s | 2H |
| | 4.5–4.8 | m | 1H |
| | 7.1–7.5 | m | 3H |

EXAMPLE No 3

(A) 2-(1-dimethylamino ethyl)pyridine

A suspension of g 1.21 (0.01 moles) of 2-acetylpyridine, 1.63 (0.02 moles) of dimethylamine hydrochloride, g 0.63 (0.01 moles) of NaCNBH3 and g 0.4 (0.01 moles) of NaOH in ml.80 of dry methanol was stirred at room temperature for 4 days. The insoluble matter was filtered off and the filtrate was made strongly alkaline with 15% aqueous NaOH. After evaporation of the mathanol, some NaOH pellets were added into the aqueous residue, and the solution was extracted with ether. The combined ethereal solutions were dried on solid NaOH and evaporated i.v. The oily residue (gr 2.8) was chromatographed on 12 g. of silicagel, eluting with CH2Cl2 containing 2% to 10% methanol. 1.7 g. of oily product were obtained, sufficiently pure for the subsequent step.

(B)

2-(1-dimethylaminoethyl)piperidine(diastereoisomeric mixture)

Gr 1.7 of 2-(1-dimethylamino ethyl) pyridine were dissolved in ml.50 CH3COOH and ml.3.6 CF3COOH, and hydrogenerated at 60 C and 3.5 atmospheres on mg.200 of PtO2. The reaction mixture was worked up as in Ex. No 1 B, and g.1.6 of yellow oil were obtained, sufficiently pure for the subsequent step.

(C)

1-(3,4-dichlorophenylacetyl)-2-(1-dimethylaminoethyl)piperidine hydrochloride—Diastereoisomer A Gr 1.6 (moles 0.01) of 2-(1-dimethylaminoethyl) piperidine and gr2.25 (moles 0.011) of 3,4-dichlorophenylacetic acid, dissolved in 20 ml. of CH2Cl2 were added with gr.3.1 (moles 0.015) of dicyclohexylcarbodiimide dissolved in 20 ml. of CH2Cl2. After 48 hours standing, the reaction mixture was worked up as in Ex. No 1 C) giving 2.8 g. of oily mixture of diastereoisomers. This was chromatographed on g.60 of silicagel, eluting with CH2Cl2 containing increasing amounts of methanol (0.2% to 1%). The fast moving diastereoisomer A was so obtained. It was dissolved in acetone and transformed into the hydrochloride by acidifying with HCl dissolved in ether. The precipitate was crystallized from acetone.

Yield gr. 1.3
C17H24Cl2N2O.HCl
M.W. 379.757
M.P. 201°-5° C.

EXAMPLE No 4

1-(3,4-dichlorophenylacetyl)-2-(1-dimethylaminoethyl) piperidine hydrochloride—Diastereoisomer B After separation of the isomer A, the elution of the column was continued, using CH2Cl2 containing increasing amounts of CH3OH (1% to 1.8%). The pure diastereoisomer B was collected, transformed into the hydrochloride in the same way as diastereoisomer A, and the salt was crystallized from acetone.

Yield g. 1.1
C17H24Cl2N2O.HCl.H2O
M.W. 397.773
M.P. 135°-41° C.

| NMR (CDCl3 - 80 MHz) | | | |
|---|---|---|---|
| delta = | 1.25 | d | 3H |
| | 1.4-1.8 | m | 6H |
| | 2.5 | s | 6H |
| | 3.2-3.6 | m | 1H |
| | 3.6-4.2 | m | 4H |
| | 4.6-4.4 | m | 1H |
| | 7.1-7.7 | m | 3H |

The threo diastereoisomer obtained as above described was resolved into its enantiomers by the following procedure: 5.37 g. (0,0157 moles) of threo 1-(3,4-dichlorophenylacetyl)-2-(1-dimethylaminoethyl)piperidine dissolved in ml 50 of dry acetone were added on stirring to a solution of 4 g. (0.016 moles) of (+)-camphor—10—sulfonic acid monohydrate dissolved in 100 ml of dry acetone; the precipitated salt was collected by suction filtration, washed with cold dry acetone and dried at 80° C.; yield g. 2.2 m.p. 228°-230° C., [α]$_D$= −27.9 C=1 EtOH. This salt was dissolved in ml 4 of warm methanol; on cooling and standing 1.1 g. of white needles, m.p. 234°-235° C., [α]$_D$=27.4 C=1 EtOH were obtained. This salt was dissolved in NaHCO3 20% and the extraction with ethyl ether gave the free base that was acidified with HCl/Ether to obtain threo (−)-1-(3,4 dichlorophenylacetyl)-2-(1-dimethylaminoethyl piperidine hydrochloride [α]$_D$= −60.7 C=1 EtOH m.p. 227°-230° C.

| An. Calcd for C17H25N2OCl3 | C | 53.76 | found | 53.60 |
|---|---|---|---|---|
| | H | 6.64 | | 6.68 |
| | N | 7.38 | | 7.29 |
| | Cl | 28.01 | | 28.10 |

The mother liquor from the first crystallization described above was evaporated i.v. and dissolved in ml 40 of warm ethyl acetate; on cooling and standing 1 g. of threo (+)-1-(3,4-dichlorophenylacetyl)-2-(1-dimethylaminoethyl) piperidine (+)-camphor-10 sulfonate was obtained and crystallized twice from ethyl acetate. The yield of camphor sulfonate salt was 0.8 g m.p. 206°-209°,[α]$_D$= +50.6 C=1 EtOH, The hydrochloride was obtained as above described=[α]$_D$= +50.6 optical purity 83% m.p. 225°-228° C.

EXAMPLE No 5

(A) 2-(alfa-amino,alfa-phenylmethyl)pyridine

Known compound, prepared by reduction (Zn in ethanolic ammonia) of 2-benzoyl pyridine (commercial product), according to Synthesis, 1976,593.

2-{alfa-[1-(2-oxopyrrolidinyl)],alfa-phenylmethyl{pyridine

Gr 3.7 (0.02 moles) of 2-(alfa-amino,alfa-phenylmethyl) pyridine were dissolved in ml.40 of CH2Cl2, together with ml2.6 (0.025 moles) of triethylamine. Ml 2.8 (0.025 moles) of 4-chlorobutyroylchloride were added, and the mixture left 1 hour at room temperature. The mixture was poured in 40 ml. of 20% Na2CO3, extracted with CH2Cl2, and the organic phase evaporated to dryness i.v. The crude oil was dissolved in 30 ml. of THF and treated with g. 0.6 (0.02 moles) of 80% NaH. After one night standing, the mixture was filtered, and the filtrate evaporated i.v. The solid residue was crystallized from hexane. M.P. 98°-100° C. Yield g 4.3

(C) 2-[alfa-phenyl,alfa-(1-pyrrolidinylmethyl)]pyridine

The amide of heading (B) was reduced to amine with LiAlH4 in THF, by the standard method. 3.2 g. of crude product were obtained, sufficiently pure for the subsequent step.

(D)

2-[alfa-phenyl,alfa-(1-pyrrolidinylmethyl)]piperidine (diastereoisomeric mixture).

Gr 3 of the pyridine derivative of heading (C) were hydrogenerated to the corresponding piperidine derivative on mg.30 of PtO2, in 60 ml. of CH3COOH. By filtering and evaporating to dryness, the product was obtained as an oil, sufficiently pure for the subsequent step.

(E)

1-(3,4—dichlorophenylacetyl)-2-[alfa-phenyl,alfa-(1-pyrrolidinylmethyl)]piperidine—Diastereoisomer A Gr 2.5 (0,01 moles) of 2 alfa-phenyl,alfa-(1-pyrrolidinylmethyl) piperidine, gr 2.3 (0.011 moles) of 3,4-dichlorophenylacetic acid and gr. 2.5 (0.012 moles) of dicyclohexylcarbodiimide in 100 ml. of CH2Cl2 were reacted by the same coupling method described in Ex. No 1 C). After being worked up in the same way, the reaction mixture yielded gr. 4 of oily diastereoisomeric mixture. The oil was dissolved in methanol, and, after 24 hour standing precipitation of isomer A took place. After filtration, the mother liquors were concentrated to dryness, and the resulting oil cromatographed on g. 50 of silicagel, eluting with CH2Cl2 containing increasing amounts of methanol (up to 3%). Another amount of isomer A was so obtained, which was combined with the first lot, and crystallized from methanol.

Yield gr. 0.9
C24H28N2OCl2
M.W. 431.394
M.P. 122°-4° C.

| NMR (CDCl3 - 80 MHz) | | | |
|---|---|---|---|
| delta = | 1.4-1.85 | m | 10H |
| | 2.25-2.6 | broad s | 5H |
| | 2.6-3 | m | 1H |
| | 3.4 | s | 2H |
| | 4.2 | d | 1H |

| NMR (CDCl3 - 80 MHz) | | |
|---|---|---|
| 5.4 | m | 1H |
| 6.4 | dd | 1H |
| 6.9–7.4 | m | 7H |

EXAMPLE No 6

1-(3,4-dichlorophenylacetyl)-2-[alfa-phenyl,alfa-(1-pyrrolidinylmethyl)]piperidine hydrochloride—Diastereoisomer B After separation of diastereoisomer A, the elution was continued using CH2Cl2 containing increasing amounts of methanol (3% to 5%). Isomer B was so obtained as an oil, which was dissolved in acetone and precipitated as the hydrochloride by adding HCl/Ether. The salt was crystallized from ethylacetate.
Yield gr. 0.7
C24H28N2OCl2.HCl
M.W. 467.859
M.P. 191°–3° C.

| NMR (CDCl3 - 80 MHz) | | | |
|---|---|---|---|
| delta = | 1.2–1.8 | m | 8H |
| | 1.9–2.4 | m | 2H |
| | 2.6–3.3 | m | 2H |
| | 3.4–4.1 | m | 6H |
| | 4.6 | dd | 1H |
| | 5.4–5.7 | m | 1H |
| | 7.1–7.8 | m | 8H |
| | 11.6 | broad peak | 1H |

EXAMPLE No 7

(A) 2-(alfa-dimethylamino,alfa-phenylmethyl)pyridine

Gr 0.9 (0.005 moles) of 2-(alfa-amino-alfa-phenylmethyl)pyridine (see Ex. No 5 A) and ml 2 (0.025 moles) of 37% aqueous formaldehyde were dissolved in ml 15 of acetonitrile, and mg 500 (0.008 moles) of NaCNBH3 were added in small portions. After 15 minutes standing, the reaction mixture was neutralized with acetic acid, and stirred for 45 more minutes. The solvent was evaporated i.v., and the oily residue partitioned between 20% aqueous NaOH and ether. The ether phase was extracted with 1N HCl, the acid extracts made alkaline with NaOH, and re-extracted with ether. Evaporation of the solvent gave gr 1.4 of oily product. The raw product of another batch (from gr 9 of starting amine) was distilled i.v.
B.P. 113°–115° C./1 mmHg.
M.P. 51°–5° C. (from hexane).

(B) 2-(alfa-dimethylamino,alfa-phenylmethyl)piperidine(-diastereoisomeric mixture)

Gr 3 of the pyridine derivative of Ex. No 7 (A) were hydrogenated at 70° C. and 3 atm. to the corresponding piperidine derivative in 30 ml CH3COOH plus 2 ml CF3COOH, on g 0.3 of PtO2. By filtration and evaporation i.v. 2.9 g. of product were obtained, sufficiently pure for the subsequent step.

(C) 1-(3,4-dichlorophenylacetyl)-2(alfa-dimethylamino,alfa-phenylmethyl)piperidine hydrochlorideDiastereoisomer A Gr 3 (0.014 moles) of 2-(alfa-dimethylamino,alfa-phenylmethyl)piperidine,gr 3.7 (0.018 moles) of 3,4-dichlorophenylacetic acid and gr.3.7 (0.018 moles) of dicyclohexylcarbodiimide in 150 ml of CH2Cl2 were reacted by the same coupling method described in Ex. No 1 C). After being worked up in the same way, 4.8 g. of oily diastereoisomeric mixture were obtained. Chromatography on gr. 100 of silicagel, eluting with CH2Cl2 containing increasing amounts of methanol (0.2% to 0.8%) gave the isomer A, as the free base, M.P. 100°–1° C. The base was transformed into the hydrochloride, by dissolving it in acetone, and acidifying with HCl/ether. The precipitated salt was crystallized from methanol/ethyl acetate.
Yield g. 0.6
C22H26CL2N2O.HCl
M.W. 441.823
M.P. 194°–5° C.

| NMR of the free base (CDCl3 - 80 MHz) | | | |
|---|---|---|---|
| delta = | 1.4–2.8 | m | 6H |
| | 2.2 | s | 6H |
| | 2.6–3 | m | 1H |
| | 3.2–3.6 | m | 1H |
| | 3.4 | s | 2H |
| | 4 | d | 1H |
| | 5.4 | m | 1H |
| | 6.3 | dd | 1H |
| | 6.9–7.4 | m | 7H |

EXAMPLE No 8

1-(3,4-dichlorophenylacetyl)-2-(alfa-dimethylamino,alfa-phenylmethyl)piperidine hydrochloride—Diastereoisomer B After separation of the diastereoisomer A, the elution of the column was continued, using CH2Cl2 containing methanol (0.8% to 1.8%). Diastereoisomer B was obtained as an oil, and transformed into the hydrochloride by dissolving in acetone and acidifying with HCl/ether. The precipitated salt was crystallized from methanol.
Yield g. 0.7
C22H26N2Cl2O.HCl
M.W. 441.823
M.P. 255°–7° C.

| NMR (CDCl3 - 80 MHz) | | | |
|---|---|---|---|
| delta = | 1.1–1.9 | m | 6H |
| | 2.7 | dd | 6H |
| | 3.5–4.2 | m | 2H |
| | 4 | q | 2H |
| | 4.6 | d | 1H |
| | 5.2 | m | 1H |
| | 7.2–7.7 | m | 8H |
| | 11.6 | broad s | 1H |

EXAMPLE 9

1-(4-nitrophenylacetyl)-2-(1-dimethylaminoethyl)-piperidine hydrochloride diastereoisomer A G. 1.7 (0.01 moles) of 2-(1-dimethylaminoethyl) piperidine and g. 3.8 (0.02 moles) of 4-nitrophenylacetic acid, dissolved in ml 30 of CH₂Cl₂ were added with g. 3 (0.015 moles) of dicyclohexylcarbodiimide dissolved in ml 20 of CH₂Cl₂ at 0° C. After standing over night, the reaction mixture was worked up as in Example 1 (C) giving 2.8 g. of an oily mixture of diastereoisomers. This was chromatographed on g. 180 of neutral aluminum oxide eluting with hexane containing increasing amounts of ethyl acetate (0.2% to 1.5%). The fast moving diastereoisomer A was so obtained. It was dissolved in acetone and transformed into the hydrochloride by acidifying with HCl dissolved in ether. The precipitate was crystallized from acetone/ethyl acetate.

Yield g. 1.8
$C_{17}H_{26}N_3O_3Cl$
M.W.=355.859
M.P.=220°–224° C.

| An. Calcd. | C | 57.38 | found | 57.10 |
|---|---|---|---|---|
| | H | 7.36 | | 7.48 |
| | N | 11.81 | | 11.31 |
| | Cl | 9.96 | | 9.74 |

I.R. (KBr): cm⁻¹ 1650; 1515; 1340; 1250.
NMR (CDCl₃): δ:1.1–1.4 m (3H); 1.6–2 m (6H); 2.5–3.2 m (7H); 3.9 s (2H); 3.6–4 m (2H); 4.9 m (1H); 7.8 AB system (4H); 11.4 broad (1H).

EXAMPLE 10

1-(4-nitrophenylacetyl)-2-(1-dimethylaminoethyl) piperidine hydrochloride diastereoisomer B After separation of the isomer A, the elution of the column was continued using hexane containing increasing amounts of ethyl acetate (1.5% to 2.5%). The pure diastereoisomer B was collected, transformed into the hydrochloride and crystallized from ethyl acetate.

Yield g. 1
$C_{17}H_{26}N_3O_3Cl$
M.W.=355.859
M.P.=209°–213° C.

| An. Calcd. | C | 57.38 | found | 57.30 |
|---|---|---|---|---|
| | H | 7.36 | | 7.38 |
| | N | 11.81 | | 11.68 |
| | Cl | 9.96 | | 9.99 |

I.R. (KBr): cm⁻¹: 1640; 1520; 1345; 1240;
NMR (CDCl₃): δ: 1.4 d (3H); 1.8 s (6H); 3.8 dd (6H); 3.1–4.2 m (3H); 4.2 AB system (2H); 4.9 m (1H); 7.9 AB system (4H); 11.2 broad (1H).

EXAMPLE 11

1-(4-bromophenylacetyl)-2-(1-dimethylaminoethyl) piperidine hydrochloride diastereoisomer A G. 2.2 (0.014 moles) of 2-(1-dimethylamino ethyl) piperidine and g. 3.9 (0.018 moles) of 4-bromophenylacetic acid, dissolved in ml 20 of CH₂Cl₂ were added at 0° C. with g. 4.6 (0.018 moles) of dicyclohexylcarbodiimide dissolved in 20 ml of CH₂Cl₂. After 48 hours standing at room temperature, the reaction mixture was worked up as in Example 1 (C) giving 4 g. of an oily mixture of distereoisomers. This was cromatographed on 60 gr. of silicagel, eluting with CH₂Cl₂ containing increasing amounts of methanol (0.5% to 1%). The fractions containing the pure diastereoisomers A were collected and evaporated i.v. to give 2.1 g. of oily product that was dissolved in methanol and acidified with HCl dissolved in ether. The precipitate was crystallized from methanol/ethyl acetate.

Yield g. 1.6
$C_{17}H_{26}N_2OBrCl$
M.W.=389.767
M.P.=225°–226° C.

| An. Calcd. | C | 52.38 | found | C | 52.19 |
|---|---|---|---|---|---|
| | H | 6.72 | | H | 6.69 |
| | N | 7.18 | | N | 7.16 |
| | Br | 20.50 | | Br | 20.37 |
| | Cl | 9.09 | | Cl | 9.15 |

I.R. (KBr): cm⁻¹: 1645; 1440; 1250; 1010.
NMR (CDCl₃): δ: 1.1 d (3H); 1.3–2 m (6H); 2.8 dd (6H); 2.3—3 m (1H); 3.6 s (2H); 3.3–4 m (2H); 4.9 m (2H); 7.2 AB system (4H); 12 broad (1H).

EXAMPLE 12

1-(4-bromophenylacetyl)-2-(1-dimethylaminoethyl) piperidine hydrochloride diastereoisomer B After separation of the isomer A, the elution of the column was continued, using CH₂Cl₂ containing increasing amounts of methanol (1.2% to 2%). The pure diastereoisomer B so obtained was transformed into the hydrochloride in the same way as diastereoisomer A. The hydrochloride was crystallized from methanol/ethyl acetate.

Yield g. 1.8
$C_{17}H_{26}N_2OBrCl$
M.W.=389.767
M.P.=221°–222° C.
I.R. (KBr): cm⁻¹: 1630; 1440; 1450; 1245; 1010.
NMR (CDCl₃): δ:1.4 d (3H); 1.5–2 m (6H); 2.8 dd (6H); 3–4.1 m (3H); 4 AB system (2H); 5 m (1H); 7.4 AB system (4H); 11.2 broad (1H).

EXAMPLE 13

1-(3-trifluoromethylphenylacetyl)-2-(1-dimethylaminoethyl) piperidine hydrochloride diastereoisomer A G. 2.2 (0.014moles) of 2-(1-dimethylaminoethyl) piperidine, dissolved in ml 40 of dry CHCl₃ were added at 0° C. with g. 3.7 (0.017 moles) of 3-trifluoromethylphenylacetyl chloride dissolved in 40 ml of dry CHCl₃. The solution obtained was stirred at room temperature over night, then was evaporated to dryness i.v., and the oily residue dissolved in ethyl acetate was extracted with 20% aqueous citric acid. The acidic solution was washed with ether and made alkaline by adding solid NaOH, the oily material separated from the basic aqueous solution was extracted with ether, dried and evaporated to oily mixture of diastereoisomers. This was chromatographed on 60 g. of silicagel, eluting with CH₂Cl₂ containing increasing amounts of methanol (0.5% to 1.2%). The fast moving diastereoisomer A so obtained was dissolved in acetone and acidified with HCl dissolved in ether. The precipitated hydrochloride was crystallized from methanol/ethyl acetate.

Yield g. 2
$C_{18}H_{26}N_2OF_3Cl$
M.W.=378.861
M.P.=154°–155° C.

| An. Calcd. | C | 57.06 | found | 56.84 |
|---|---|---|---|---|
| | H | 6.92 | | 6.94 |
| | N | 7.39 | | 7.23 |

| | Cl | 15.04 | | 14.75 |
| --- | --- | --- | --- | --- |
| | F | 9.36 | | 9.26 |

I.R. (KBr): cm$^{-1}$: 1650; 1340; 1130; 1010.

NMR (CDCl$_3$): δ: 1.2 d (3H); 1.5–1.9 (6H); 2.8 dd (6H); 2.4–3.2 m (2H); 3.9 s (2H); 3.4–4 m (1H); 5 m (1H) 7.3–7.7 m (4H); 12 broad (1H).

EXAMPLE 14

1-(3-trifluoromethylphenylacetyl)-2-(1-dimethylaminoethyl) piperidine hydrochloride diastereoisomer B After separation of the isomer A, the elution of the column was continued, using CH$_2$CL$_2$ containing increasing amounts of CH$_3$OH (1.4% to 2%). The pure diastereoisomer B so obtained was dissolved in acetone and acidified with HCl dissolved in ether. The precipitated hydrochloride was crystallized from acetone.

Yield g. 1.6
C$_{18}$H$_{26}$N$_2$OF$_3$Cl
M.W.=378.861
M.P.=237°–238°

| An. Calcd. | C | 57.06 | found | 56.88 |
| --- | --- | --- | --- | --- |
| | H | 6.92 | | 6.88 |
| | N | 7.39 | | 7.33 |
| | F | 15.04 | | 15.12 |
| | Cl | 9.36 | | 9.40 |

I.R. (KBr): cm$^{-1}$: 1635; 1460; 1340; 1120.

NMR (CDCl$_3$): 1.3 d (3H); 1.4–2 m (6H); 2.9 dd (6H); 3.1–4 m (3H); 4.2 AB system (2H); 5 m (1H); 7.3–7.7 m (4H); 11.4 broad (1H).

EXAMPLE 15

1-(4-trifluoromethylphenylacetyl)-2-(1-dimethylaminoethyl) piperidine hydrochloride diastereoisomer A G. 1.8 (0.012 moles) of 2-(1-dimethylaminoethyl)-piperidine dissolved in ml 20 of dry CHCl$_3$ were added at 0° C. to gr. 3.7 (0.017 moles) of 4-trifluoromethylphenyl acetyl chloride dissolved in ml 20 of dry CHCl$_3$. The solution obtained was stirred at room temperature overnight and evaporated to dryness i.v.; the oily residue was worked up as in Example 13 giving 4.2 g. of oily mixture diastereoisomers. This was cromatographed on 80 g. of silicagel, eluting with CH$_2$Cl$_2$ containing increasing amounts of methanol (0.5% to 2%). The fast moving diastereoisomer A so obtained was dissolved in acetone and acidified with HCl dissolved in ether. The precipitated hydrochloride was crystallized from ethyl acetate.

Yield g. 1.8
C$_{18}$H$_{26}$N$_2$OF$_3$Cl
M.W.=378.861
M.P.=213°–214° C.

| An. Calcd. | C | 57.06 | found | 56.93 |
| --- | --- | --- | --- | --- |
| | H | 6.92 | | 6.93 |
| | N | 7.39 | | 7.35 |
| | F | 15.04 | | 15.00 |
| | Cl | 9.36 | | 9.35 |

I.R.: (KBr): cm$^{-1}$: 1650; 1440; 1325; 1100.

EXAMPLE 16

1-(4-trifluoromethylphenylacetyl)-2-(1-dimethylaminoethyl) piperidine hydrochloride diastereoisomer B monohydrate After separation of the isomer A, the elution of the column was continued, using CH$_2$Cl$_2$ containing increasing amounts of CH$_3$OH (2% to 4%). The pure diastereoisomer B obtained was transformed into the hydrochloride in the same way as diastereoisomer A. The hydrochloride was crystallized from ethyl acetate/ethyl ether.

Yield g. 1.4
C$_{18}$H$_{26}$N$_2$OF$_3$Cl·H$_2$O
M.W.=396.877
M.P.=204°–206°

| An. Calcd. | C | 54.57 | found | 54.80 |
| --- | --- | --- | --- | --- |
| | H | 6.60 | | 6.76 |
| | N | 7.06 | | 7.11 |
| | F | 14.36 | | 14.40 |
| | Cl | 8.94 | | 8.99 |

I.R. (KBr): cm$^{-1}$: 1640; 1440; 1325; 1105.

EXAMPLE 17

1-(5,6,7,8-tetrahydro-2-naphtylacetyl)-2-(1-dimethylaminoethyl) piperidine hydrochloride diastereoisomer A monohydrate G. 1.8 (0.012 moles) of 2-(1-dimethylaminoethyl)-piperidine dissolved in ml 20 of dry CHCl$_3$ were added at 0° C. to 3.75 (0.018 moles) of 5,6,7,8-tetrahydro-2-naphtylacetyl chloride dissolved in ml 20 of dry CHCl$_3$, and stirred at room temperature overnight. The resulting reaction mixture was worked up as in Example 15, giving g. 3.1 of oily mixture of diastereoisomers. This was chromatographed on 120 g. of silicagel, eluting with CH$_2$Cl$_2$ containing increasing amounts of methanol (0.1% to 1.2%). The fast moving diastereoisomer A so obtained was dissolved in acetone and acidified with HCl dissolved in ether. The precipitated hydrochloride was crystallized from acetone.

Yield g. 1.5
C$_{21}$H$_{33}$N$_2$OCl·H$_2$O
M.W.=382.963
M.P.=146°–148° C.

| An. Calcd. | C | 65.79 | found | 65.93 |
| --- | --- | --- | --- | --- |
| | H | 9.13 | | 9.08 |
| | N | 7.31 | | 7.35 |
| | Cl | 9.26 | | 9.40 |

I.R. (KBr): cm$^{-1}$: 1640; 1440; 1250; 1240; 1010

EXAMPLE 18

1-(5,6,7,8-tetrahydro-2-naphtylacetyl)-2-(1-dimethylaminoethyl) piperidine hydrochloride diastereoisomer B monohydrate After separation of the isomer A, the elution of the column was continued, using CH$_2$Cl$_2$ containing increasing amounts of methanol (1.4% to 1.8%). The diastereoisomer B was treated with HCl/ether to give the hydrochloride which was recrystallized from ethyl acetate.

Yield g. 1.3
C$_{21}$H$_{33}$N$_2$OCl·H$_2$O

M.W.=382.963
M.P.=199°-203°

| An. Calcd. | C | 65.79 | found | 66.06 |
|---|---|---|---|---|
| | H | 9.13 | | 8.96 |
| | N | 7.31 | | 7.32 |
| | Cl | 9.26 | | 9.21 |

I.R. (KBr): cm$^{-1}$: 1650; 1410; 1230; 1030.

EXAMPLE 19

1-(3,4-dichlorophenylacetyl)-2-(1-methylpyrrolidin-2-yl)-piperidine hydrochloride emihydrate diastereoisomer A G. 1.7 (0.01 moles) of 2-(1-methylpyrrolidin-2-yl)-piperidine, dissolved in ml 40 of dry CHCl$_3$ were added at 0° C. with g. 2.9 (0.013 moles) of 3,4-dichlorophenylacetyl chloride dissolved in 40 ml of dry CHCl$_3$. The solution obtained was stirred at room temperature over night and evaporated to dryness i.v. The oily residue dissolved in ethyl acetate was extracted with 20% aqueous citric acid. The acidic solution was washed with ether and made alkaline by NaOH, the aqueous solution was extracted with ether, dried and evaporated to oily mixture of diastereoisomers. These were chromatographed on 40 g. of silicagel, eluting with CH$_2$Cl$_2$ containing increasing amounts of methanol (0.5 to 2%). The diastereoisomer A so obtained was dissolved in acetone and acidified with HCl dissolved in ether.

The precipitated hydrochloride was crystallized from methanol/ethyl acetate.
Yield g. 0.3
C$_{18}$H$_{25}$N$_2$OCl$_3$·½H$_2$O
M.W.=400.775
M.P.=165°-70°

| An. Calcd. | C | 53.94 | found | 54.13 |
|---|---|---|---|---|
| | H | 6.53 | | 6.45 |
| | N | 6.99 | | 6.96 |
| | Cl | 26.54 | | 26.27 |

IR (KBr): cm$^{-1}$: 1640; 1440; 1240; 1030.
NMR (CDCl$_3$): δ: 1.3-1.9 m (6H); 1.9-2.4 m (4H); 2.8 s (3H) 3.2-4.6 m (7H) 4.7-5.1 m (1H) 7.2-7.5 m (3H).

The diastereoisomer B was obtained from the mother liquors by fractional crystallisation as its hydrochloride.
C$_{18}$H$_{25}$N$_2$OCl$_3$
M.W.=391.767
M.P.=173°-178°

| An. Calcd. | C | 55.18 | | 55.37 |
|---|---|---|---|---|
| | H | 6.43 | | 6.19 |
| | N | 7.15 | | 7.02 |
| | Cl | 27.15 | | 26.94 |

IR (KBr): cm$^{-1}$: 1635; 1440; 1210.
NMR (CDCl$_3$): δ1.2-2 m (6H); 2-2.4 m (4H); 2.9 s (3H) 3.2-4.6 m (7H) 4.8-5.3 m (1H) 7.2-7.5 m (3H).

EXAMPLE 20

1-(3,4-dichlorophenylacetyl)-2-(1-methylpiperidin-2-yl)-piperidine hydrochloride diastereoisomer A G. 5.2 (0.028 moles) of 2-(1-methyl-2-piperidinyl)-piperidine, dissolved in ml 60 of dry CHCl were added at 0° C. with g. 6.7 (0.03 moles) of 3,4-dichlorophenylacetyl chloride dissoved in 60 ml of dry CHCl$_3$. The solution obtained was stirred at room temperature over night, then evaporated to dryness i.v., dissolving the oily residue in ethyl acetate. After extraction with 20% aqueous citric acid. The acidic solution was washed with ether and made alkaline by adding solid NaOH. The oily material separated from the basic aqueous solution was extracted with ether, dried and evaporated to oily mixture of diastereoisomers.

This was chromatographed on 100 g. of silicagel, eluting with hexane containing increasing amounts of Ethyl acetate. The fast moving diastereoisomer A so obtained was dissolved in acetone and acidified with HCl dissolved in ether. The precipitate hydrochloride was crystallized from methanol/ethyl acetate.
Yield g. 0.9
C$_{19}$H$_{27}$N$_2$OCl$_3$
M.W.=405.793
M.P.=207°-210° C.

| An. Calcd. | C | 56.23 | found | 55.96 |
|---|---|---|---|---|
| | H | 6.65 | | 6.74 |
| | N | 6.90 | | 6.84 |
| | Cl | 26.21 | | 26.01 |

IR (KBr): cm$^{-1}$: 1625; 1450; 1140.
NMR (CDCl$_3$): δ1.3 m (6H); 1.6 m (7H); 2.9-2.3 m (1H) 2.4 s (3H); 2.7-3.2 m (3H); 3.7 s (2H) 4.9 m (1H); 7-7.4 m (3H).

EXAMPLE 21

1-(3,4-dichlorophenylacetyl)-2-(1-methylpiperidin-2-yl)-piperidine hydrochloride monohydrate diastereoisomer B After separation of the isomer A, the elution of the column was continued, using hexane contaning increasing amounts of ethyl acetate. The pure diastereoisomer B so obtained was dissolved in acetone and acidified with HCl dissolved in ether. The precipitate hydrochloride was crystallized from acetone.
Yield g. 0.8
C$_{19}$H$_{27}$N$_2$OCl$_3$·H$_2$O
M.W.=423.809
M.P.=194°-96° C.

| An. Calcd. | C | 53.79 | found | 53.76 |
|---|---|---|---|---|
| | H | 6.84 | | 6.88 |
| | N | 6.60 | | 6.82 |
| | Cl | 25.12 | | 25.33 |

IR (KBr): cm$^{-1}$ 1620; 1450; 1150.
NMR (CDCl$_3$): δ1.3-1.8 m (12H); 2.4 s (3H); 2.5-2.7 m (1H) 2.7-3.3 m (4H); 3.4-3.7 m (2H); 3.7 s (3H) 4.7-5 m (1H); 7.1-7.5 m (3H).

EXAMPLE 22

2-(1-Methyl-2-piperidinyl)-piperidine 6.5 g (0.019 moles) of 2-(1-methyl-2-piperidinyl)-piperidine were dissolved in 100 ml of Isoamyl alcohol at 50° c. 3.3 g (0.0143 moles) of sodium were added under nitrogen, and the reaction was refluxed for 4 hours, cooled to 50° C. and 30 ml of EtOH added.

The resulting solution was quenched in water, extracted with ether, evaporated, to yield 5.2 g of yellow oil, which was used for the subsequent reaction without further purification.

Analogously, 2-(1-methyl-2-pyrrolidinyl)-piperidine, was prepared.

The compounds of Examples 1 to 21 are summarised in the following Table I.

TABLE I

General Formula $$\begin{array}{c} R_x \\ | \\ CH-NR_1R_2 \end{array}$$ attached to 2-position of piperidine with N-CO-R

| Example No. | R | $R_1 R_2$ | $R_x$ | Salt | Molecular Formula | Molecular Weight | Melting Point (°C.) |
|---|---|---|---|---|---|---|---|
| 1 | -CH₂-(2,4-dichlorophenyl) | $R_1R_2$ = (pyrrolidinyl ring) | —CH₃ | — | $C_{19}H_{26}Cl_2N_2O$ | 369.33 | 94–6 |
| 2 | " | " | " | — | $C_{19}H_{26}Cl_2N_2O$ | 369.33 | 86–7 |
| 3 | " | $R_1, R_2 = CH_3$ | —CH₃ erithro | HCl | $C_{17}H_{24}Cl_2N_2O.HCl$ | 379.757 | 201–5 |
| 4 | " | " | —CH₃ threo | HCl.H₂O | $C_{17}H_{24}Cl_2N_2O.HCl.H_2O$ | 397.773 | 135–41 |
| " | " | " | threo (−) | HCl | $C_{17}H_{24}Cl_2N_2O.HCl$ | 379.757 | 227–30 |
| " | " | " | thero (+) | HCl | $C_{17}H_{24}Cl_2N_2O.HCl$ | 379.757 | 225–28 |
| 5 | " | $R_1R_2$ = (piperidinyl + phenyl) | — | — | $C_{24}H_{28}Cl_2N_2O$ | 431.394 | 122–4 |
| 6 | " | " | " | HCl | $C_{24}H_{28}Cl_2N_2O.HCl$ | 467.859 | 191–3 |
| 7 | " | $R_1, R_2 = CH_3$ | " | HCl | $C_{22}H_{26}Cl_2N_2O.HCl$ | 441.823 | 194–5 |
| 8 | " | " | " | HCl | $C_{22}H_{26}Cl_2N_2O.HCl$ | 441.823 | 255–7 |
| 9 | -CH₂-(4-nitrophenyl) | $R_1 = R_2 = CH_3$ | CH₃ | HCl | $C_{17}H_{25}N_3O_3.HCl$ | 355.859 | 220–4 |
| 10 | " | " | " | HCl | $C_{17}H_{25}N_3O_3.HCl$ | 355.859 | 209–13 |
| 11 | -CH₂-(4-bromophenyl) | $R_1 = R_2 = CH_3$ | CH₃ | HCl | $C_{17}H_{25}N_2OBr.HCl$ | 389.767 | 225–6 |
| 12 | " | " | " | HCl | $C_{17}H_{25}N_2OBr.HCl$ | 389.767 | 221–2 |
| 13 | -CH₂-(3-trifluoromethylphenyl) | " | " | HCl | $C_{18}H_{25}N_2OF_3.HCl$ | 378.861 | 154–5 |
| 14 | " | " | " | HCl | $C_{18}H_{25}N_2OF_3.HCl$ | 378.861 | 237–8 |
| 15 | -CH₂-(4-trifluoromethylphenyl) | " | " | HCl | $C_{18}H_{25}N_2OF_3.HCl$ | 378.861 | 213–4 |
| 16 | " | " | " | HCl.H₂O | $C_{18}H_{25}N_2OF_3.HCl.H_2O$ | 396.877 | 204–6 |
| 17 | -CH₂-(tetrahydronaphthyl) | " | " | HCl.H₂O | $C_{21}H_{32}N_2O.HCl.H_2O$ | 382.963 | 146–8 |

TABLE I-continued

General Formula $$\begin{array}{c} R_x \\ | \\ CH-NR_1R_2 \end{array}$$ (on cyclohexane ring with N-CO-R)

| Example No. | R | R₂ | R₁, Rₓ | Salt | Molecular formula | Molecular weight | Melting point (°C) |
|---|---|---|---|---|---|---|---|
| 18 | " | " | " | HCl.H₂O | $C_{21}H_{32}N_2O \cdot HCl \cdot H_2O$ | 382.963 | 199–203 |
| 19 | CH₂-C₆H₃Cl₂ (3,4-dichlorobenzyl) | CH₃ | —(CH₂)₃— | HCl.½H₂O | $C_{18}H_{25}N_2OCl_3 \cdot \tfrac{1}{2}H_2O$ | 400.775 | 165°–170° |
|  | " | CH₃ | —(CH₂)₃— | HCl | $C_{18}H_{25}N_2OCl_3$ | 391.767 | 173°–178° |
| 20 | " | CH₃ | —(CH₂)₄— | HCl | $C_{19}H_{27}N_2OCl$ | 405.793 | 207°–10° |
| 21 | " | CH₃ | —(CH₂)₄— | HCl.H₂O | $C_{19}H_{27}N_2OCl_3 \cdot H_2O$ | 423.809 | 194°–96° |

The pharmacological activity of the compounds of this invention is illustrated by various in vitro and in vivo models, using the following test procedures, in which the mouse tail flick test demonstrate analgesic activity.

The results of the tests are given in Table 2.

Mouse Tail-flick test (Modified from the procedure published by D'Amour et al., J. Pharm. Exptl. Ther. 72, 74/1941).

Male Charles River mice, average weight 26 g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml. Kg⁻¹. 30 min later mice are placed again under heat source (Socrel apparatus) and reaction time is recorded.

The analgestic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

RECEPTOR AFFINITY STUDY

Tissue preparation

Radio receptor binding to μ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000 ×g×10 min.

The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to μ sites (Magnan J., 1982)

³H [D-Ala², MePhe⁴, Gly-ol⁵] Enkephalin (³H—DAGO), an enkephalin analogue that binds selectively to μ receptor, is added to the biological substrate and incubated at 25° C. for 40 min., filtered through Whatman GF-C and washed with ice-cold Tris-buffer.

The filters are then dryed, solubilized in Filtercount and the radioactivity monitored. Non specific binding is determined in the presence of 10⁻⁶M Naloxone.

Binding to K sites (Magnan J., 1982)

The binding of tritiated Ethylketocyclazocine to brain homogenate is measured the in presence of 100 nanomolar D-Ala-D-LeuEnkephalin (DADLE) and 100 nanomolar DAGO, added to saturate the δ and μ opioid receptors respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

MR 2266.500 nM is utilized to determine the saturable binding.

For the calculation of the kinetic parameters of the binding of labelled and unlabelled ligands, the equilibrium dissociation constant ($K_D$), the inhibition constant (Ki) and the maximum number of binding sites (B max) are determined from saturation curves and competition experiments (Hill 1910; Scatchard 1949; Cheng and Prusoff 1973; Gillan et al. 1980).

A concentration of radioligand near $K_D$ is used in the binding assays evaluating our compounds.

Hill, A. V. (1910): J. Physiol.40, IV–VIII (1910)
Scatchard G. (1949): Ann. N.Y. Acad. Sci., 51, 660–674
Cheng and Prusoff W. H. (1973): Biochem. Pharmac. 22, 3099–3102
Gillan M. G. C., Kosterlitz H. W. and Paterson S. Y. (1980): Br. J. Pharmac. 70, 481–490
Kotsterliz H.W., Paterson S.Y. and Robson L. E. (1981): Br. J. Pharmac. 73, 939–949
Magnan J., Paterson S. Y., Tavani A., and Kosterlits H.W. (1982): Arch. Pharmacol. 319, 197–205

TABLE 2

| Example No. | Mouse tail-flick ED₅₀ (mg.kg⁻¹s.c.) | Receptor binding ($k_j = nM$) | |
|---|---|---|---|
|  |  | μ | k |
| 2 | 4.12 |  |  |
| 4 | 0.41 (0.75 p.o.) | 913 | 2.3 |

We claim:

1. A compound, or a solvate or salt thereof, of formula I:

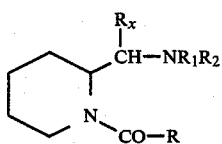

in which:
R$_1$ and R$_2$ are each hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms or together form polymethylene of 3 to 6 carbon atoms or alkenylene of 4 carbon atoms, provided that R$_1$ and R$_2$ are not simultaneously hydrogen;
Rx is alkyl of 1 to 6 carbon atoms or phenyl, or Rx together with R$_1$ form a —(CH$_2$)$_3$— or —(CH$_2$)$_4$— group; and
R has the formula II

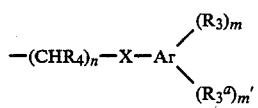

in which
n is 0, 1 or 2,
m is 0, 1 or 2,
m' is 0, 1 or 2, provided m+m' is equal to or less than 2;
X is a direct bond or O, S or NR$_5$ in which R$_5$ is hydrogen or alkyl or 1 to 6 carbon atoms,
Ar is phenyl and each of R$_3$ and R$_3{}^a$ is nitro, cyano, alkoxy of 1 to 6 carbon atoms, alkyl of 1 to 6 carbon atoms, haloalkoxy of 1 to 6 carbon atoms, haloalkyl of 1 to 6 carbon atoms, haloalkenyl of 2 to 6 carbon atoms, haloalkynyl of 2 to 6 carbon atoms, or halogen, or, when m is 2, and m' is 0 two R$_3$'s form polymethylene of 3 to 6 carbon atoms, or each of R$_3$ and R$_3{}^1$ is —COOR$_6$, —CONR$_7$R$_8$, —SO$_3$$_{R9}$, —SO$_2$NR$_{10}$R$_{11}$ or —COR$_{12}$, wherein R$_6$, R$_7$, R$_8$, R$_9$, R$_{10}$, R$_{11}$ and R$_{12}$ are independently hydrogen or alkyl of 1 to 6 carbon atoms; and
R$_4$ is hydrogen or alkyl of 1 to 6 carbon atoms.

2. A compound according to claim 1, in which each of R$_1$ and R$_2$ is methyl, ethyl, propyl, butyl, pentyl or hexyl.

3. A compound according to claim 1, in which R$_1$ and R$_2$ together form a propylene, butylene, pentylene or hexylene group, or a —CH$_2$—CH=CH—CH$_2$— group.

4. A compound according to claim 5 in which R$_3$ or R$_3{}^a$ is chlorine, bromine, NO$_2$ or CF$_3$ in the meta- or para-position, or R$_3$ and R$_3{}^a$ are both chlorine in the meta-and para-positions.

5. A compound selected from the group consisting of:
1-(3,4-dichlorophenylacetyl)-2-[1-(1-pyrrolidinyl)ethyl] piperidine—Diastereoisomer A,
1-(3,4-dichlorophenylacetyl)-2-[1-(1-pyrrolidinyl)]ethyl piperidine—Diastereoisomer B,
1-(3,4-dichlorophenylacetyl)-2-(1-dimethylaminoethyl)piperidine—Diastereoisomer A,
1-(3,4-dichlorophenylacetyl)-2-(1-dimethylaminoethyl) piperidine—Diastereoisomer B.
Threo (−)-1-(3,4-dichlorophenylacetyl)-2-(1-dimethylaminoethyl) piperidine.
Threo (+)-1-(3,4-dichlorophenylacetyl)-2-(1-dimethylaminoethyl) piperidine,
1-(3,4-dichlorophenylacetyl)-2-[alfa-phenyl, alfa-(1-pyrrolidinylmethyl)] piperidine—Diastereoisomer A,
1-(3,4-dichlorophenylacetyl)-2-[alfa-phenyl, alfa-(1-pyrrolidinylmethyl)] piperidine—Diastereoisomer B,
1-(3,4-dichlorophenylacetyl)-2-(alfa-dimethyl amino, alfa-phenylmethyl) piperidine Diastereoisomer A,
1-(3,4-dichlorophenylacetyl)-2-(alfa-dimethylamino, alfa-phenylmethyl) piperidine—Diastereoisomer B,
1-(4-nitrophenylacetyl)-2-(1-dimethylaminoethyl) piperidine—Diastereoisomer A,
1-(4-nitrophenylacetyl)-2-(1-dimethylaminoethyl) piperidine—Diastereoisomer B,
1-(4-bromophenylacetyl)-2-(1-dimethylaminoethyl) piperidine—Diastereoisomer A,
1-(4-bromophenylacetyl)-2-(1-dimethylaminoethyl) piperidine—Diastereoisomer B,
1-(3-trifluoromethylphenylacetyl)-2-(1-dimethylaminoethyl) piperidine—Diastereoisomer A,
1-(3-trifluoromethylphenylacetyl)-2-(1-dimethylaminoethyl) piperidine—Diastereoisomer B,
1-(4-trifluoromethylphenylacetyl)-2-(1-dimethylaminoethyl) piperidine—Diastereoisomer A,
1-(4-trifluoromethylphenylacetyl)-2-(1-dimethylaminoethyl) piperidine—Diastereoisomer B,
1-(5,6,7,8-tetrahydro-2-naphthylacetyl)-2-(1-dimethylaminoethyl) piperidine—Diastereoisomer A,
1-(5,6,7,8-tetrahydro-2-naphthylacetyl)-2-(1-dimethylaminoethyl) piperidine—Diastereoisomer B,
1-(3,4-dichlorophenylacetyl)-2-(1-methylpyrrolidin-2-yl) piperidine—Diastereoisomer A,
1-(3,4-dichlorophenylacetyl)-2-(1-methylpiperidin-2-yl) piperidine—Diastereoisomer A, and
1-(3,4-dichlorophenylacetyl)-2-(1-methylpiperidin-2-yl) piperidine—Diastereoisomer B, 6. A compound of formula (III):

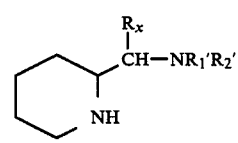

in which R' and R'$_2$ are R$_1$ and R$_2$ as defined in claim 1, or each is a group or atom convertible to R$_1$ and R$_2$, and Rx is as defined in claim 1.

7. The compound according to claim 1, wherein said haloalkyl is —CF$_3$ and said haloalkoxy is —OCF$_3$, —OCHF$_2$, —OCF$_2$CF$_2$H or —OCCl$_2$CF$_3$.

8. A pharmaceutical composition useful for effecting analgesia in mammals which comprises an analgesically effective amount of a compound of the formula I:

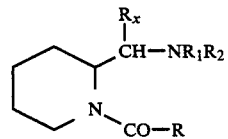

or a solvate or a pharmaceutically acceptable salt thereof wherein R$_1$ and R$_2$ are each hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms or together form polymethylene of 3 to 6 carbon atoms or alkenylene of 4 carbon atoms, provided that $R_1$ and $R_2$ are not simultaneously hydrogen;

Rx is alkyl of 1 to 6 carbon atoms or phenyl, or Rx together with $R_1$ form a —(CH$_2$)$_3$— or —(CH$_2$)$_4$— group; and R has the formula II

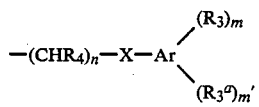  (II)

in which n is 0, 1 or 2, m is 0, 1 or 2, m' is 0, 1 or 2, provided m + m' is equal to or less than 2;

X is a direct bond or O, S or NR$_5$ in which R$_5$ is hydrogen or alkyl or 1 to 6 carbon atoms, Ar is phenyl and each of $R_3$ and $R_3^a$ is nitro, cyano, alkoxy of 1 to 6 carbon atoms, alkyl of 1 to 6 carbon atoms, haloalkoxy of 1 to 6 carbon atoms, haloalkyl of 1 to 6 carbon atoms, haloalkenyl of 2 to 6 carbon atoms, haloalkynyl of 2 to 6 carbon atoms, or halogen, or, when m is 2, and m' is 0 two $R_3$'s form polymethylene of 3 to 6 carbon atoms, or each of $R_3$ and $R_3^a$ is —COOR$_6$, —CONR$_7$R$_8$, —SO$_3$R$_9$, —SO$_2$NR$_{10}$R$_{11}$ or —COR$_{12}$, wherein R$_6$, R$_7$, R$_8$, R$_9$, R$_{10}$, R$_{11}$ and R$_{12}$ are independently hydrogen or alkyl of 1 to 6 carbon atoms; and R$_4$ is hydrogen or alkyl of 1 to 6 carbon atoms; in combination with a pharmaceutically acceptable carrier therefor.

9. A composition according to claim 8 in which each of $R_1$ and $R_2$ is methyl, ethyl, propyl, butyl, pentyl or hexyl.

10. A composition according to claim 8 in which $R_1$ and $R_2$ together form a propylene, butylene, pentylene or hexylene group or a —CH$_2$—CH=CH—CH$_2$ group.

11. A composition according to claim 8 in which $R_3$ and $R_3^a$ are both chlorine in the meta- and para- positions.

12. A composition according to claim 8 wherein the compound is selected from the group consisting of:

1-(3,4-dichlorophenylacetyl)-2-[1-pyrrolidinyl)ethyl] piperidine—Diastereoisomer A, 1-(3,4-dichlorophenylacetyl)-2-[1-(1-pyrrolidinyl)]ethyl piperidine—Diastereoisomer B, 1-(3,4-dichlorophenylacetyl)-2-(1-dimethylaminoethyl)piperidine—Diastereoisomer A, 1-(3,4-dichlorophenylacetyl)-2-(1-dimethylaminoethyl) piperidine—Diastereoisomer B.

Threo (—)-1-(3,4-dichlorophenylacetyl)-2-(1-dimethylaminoethyl) piperidine.

Threo (+)-1-(3,4-dichlorophenylacetyl)-2-(1-dimethylaminoethyl) piperidine, 1-(3,4-dichlorophenylacetyl)-2-[alfa-phenyl, alfa-(1-pyrrolidinylmethyl)] piperidine—Diastereoisomer A, 1-(3,4-dichlorophenylacetyl)-2-[alfa-phenyl, alfa-(1-pyrrolidinylmethyl)] piperidine—Diastereoisomer B, 1-(3,4-dichlorophenylacetyl)-2-(alfa-dimethyl amino, alfa-phenylmethyl) piperidine Diastereoisomer A, 1-(3,4-dichlorophenylacetyl)-2-(alfa-dimethylamino, alfa-phenylmethyl) piperidine—Diastereoisomer B, 1-(4-nitrophenylacetyl)-2-(1-dimethylaminoethyl) piperidine—Diastereoisomer A, 1-(4-nitrophenylacetyl)-2-(1-dimethylaminoethyl) piperidine—Diastereoisomer B, 1-(4-bromophenylacetyl)-2-(1-dimethylaminoethyl) piperidine—Diastereoisomer A, 1-(4-bromophenylacetyl)-2-(1-dimethylaminoethyl) piperidine—Diastereoisomer B, 1-(3-trifluoromethylphenylacetyl)-2-(1-dimethylaminoethyl) piperidine—Diastereoisomer A, 1-(3-trifluoromethylphenylacetyl)-2-(1-dimethylaminoethyl) piperidine—Diastereoisomer B, 1-(4-trifluoromethylphenylacetyl)-2-(1-dimethylaminoethyl) piperidine—Diastereoisomer A, 1-(4-trifluoromethylphenylacetyl)-2-(1-dimethylaminoethyl) piperidine—Diastereoisomer B, 1-(5,6,7,8-tetrahydro-2-naphthylacetyl)-2-(1-dimethylaminoethyl) piperidine—Diastereoisomer A, 1-(5,6,7,8-tetrahydro-2-naphthylacetyl)-2-(1-dimethylaminoethyl) piperidine—Diastereoisomer B, 1-(3,4-dichlorophenylacetyl)-2-(1-methylpyrrolidin-2-yl) piperidine—Diastereoisomer A, 1-(3,4-dichlorophenylacetyl)-2-(1-methylpiperidin-2-yl) piperidine—Diastereoisomer A, and 1-(3,4-dichlorophenylacetyl)-2-(1-methylpiperidin-2-yl) piperidine—Diastereoisomer B, 13. The composition according to claim 8, wherein said haloalkyl is —CF$_3$ and said haloalkoxy is —OCF$_3$, —OCHF$_2$, —)CF$_2$CF$_2$H or —OCCl$_2$CF$_3$.

14. A method of treating pain in mammals which comprises administering to a mammal in need thereof an analgesically effective amount of a compound of the formula I:

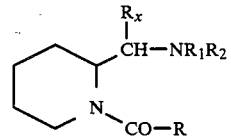  I or a solvate or a pharmaceutically acceptable salt thereof wherein $R_1$ and $R_2$ are each hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms or together form polymethylene of 6 to 6 carbon atoms or alkenylene of 4 carbon atoms, provided that $R_1$ and $R_2$ are not simultaneously hydrogen;

Rx is alkyl of 1 to 6 carbon atoms or phenyl, or Rx together with $R_1$ form a —(CH$_2$)$_3$— or —(CH$_2$)$_4$— group; and R has the formula II

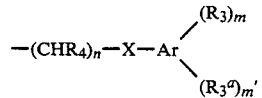  (II)

in which n is 0, 1 or 2, m is 0, 1 or 2, m' is 0, 1 or 2, provided m + m' is equal to or less than 2;

X is a direct bond or O, S or NR$_5$ in which R$_5$ is hydrogen or alkyl or 1 to 6 carbon atoms, Ar is phenyl and each of $R_3$ and $R_3^a$ is nitro, cyano, alkoxy of 1 to 6 carbon atoms, alkyl of 1 to 6 carbon atoms, haloalkoxy of 1 to 6 carbon atoms, haloalkyl of 1 to 6 carbon atoms, haloalkenyl of 2 to 6 carbon atoms, haloalkynyl of 2 to 6 carbon atoms, or halogen, or, when m is 2, and m' is 0 two $R_3$'s form polymethylene of 3 to 6 carbon atoms, or each of $R_3$ and $R_3{}^a$ is —$COOR_6$, —$CONR_7R_8$, —$SO_3R_9$, —$SO_2NR_{10}R_{11}$ or —$COR_{12}$, wherein $R_6$, $R_7$, $R_8$, $R_9$, $R_{10}$, $R_{11}$ and $R_{12}$ are independently hydrogen or alkyl of 1 to 6 carbon atoms; and $R_4$ is hydrogen or alkyl of 1 to 6 carbon atoms.

15. A method according to claim 2 in which each of $R_1$ and $R_2$ is methyl, ethyl, propyl, butyl, pentyl or hexyl.

16. A method according to claim 14 in which $R_1$ and $R_2$ together form a propylene, butylene, pentylene or hexylene group or a —$CH_2$—$CH$=$CH$—$CH_2$ group.

17. A method according to claim 14 in which $R_3$ and $R_3{}^a$ are both chlorine in the meta- and para- positions.

18. A method according to claim 14 wherein the compound is selected from the group consisting of:
1-(3,4-dichlorophenylacetyl)-2-[1-(1-pyrrolidinyl)ethyl] piperidine—Diastereoisomer A,
1-(3,4-dichlorophenylacetyl)-2-[1-(1-pyrrolidinyl)ethyl] piperidine—Diastereoisomer B,
1-(3,4-dichlorophenylacetyl)-2-(1-dimethylaminoethyl) piperidine—Diastereoisomer A,
1-(3,4-dichlorophenylacetyl)-2-(1-dimethylaminoethyl) piperidine—Diastereoisomer B.
Threo (—)-1-(3,4-dichlorophenylacetyl)-2-(1-dimethylaminoethyl) piperidine.
Threo (+)-1-(3,4-dichlorophenylacetyl)-2-(1-dimethylaminoethyl) piperidine,
1-(3,4-dichlorophenylacetyl)-2-[alfa-phenyl, alfa-(1-pyrrolidinylmethyl)] piperidine—Diastereoisomer A,
1-(3,4-dichlorophenylacetyl)-2-[alfa-phenyl, alfa-(1-pyrrolidinylmethyl)] piperidine—Diastereoisomer B,
1-(3,4-dichlorophenylacetyl)-2-(alfa-dimethyl amino, alfa-phenylmethyl) piperidine Diastereoisomer A,
1-(3,4-dichlorophenylacetyl)-2-(alfa-dimethylamino, alfa-phenylmethyl) piperidine—Diastereoisomer B,
1-(4-nitrophenylacetyl)-2-(1-dimethylaminoethyl) piperidine—Diastereoisomer A,
1-(4-nitrophenylacetyl)-2-(1-dimethylaminoethyl) piperidine—Diastereoisomer B,
1-(4-bromophenylacetyl)-2-(1-dimethylaminoethyl) piperidine—Diastereoisomer A,
1-(4-bromophenylacetyl)-2-(1-dimethylaminoethyl) piperidine—Diastereoisomer B,
1-(3-trifluoromethylphenylacetyl)-2-(1-dimethylaminoethyl) piperidine—Diastereoisomer A,
1-(3-trifluoromethylphenylacetyl)-2-(1-dimethylaminoethyl) piperidine—Diastereoisomer B,
1-(4-trifluoromethylphenylacetyl)-2-(1-dimethylaminoethyl) piperidine—Diastereoisomer A,
1-(4-trifluoromethylphenylacetyl)-2-(1-dimethylaminoethyl) piperidine—Diastereoisomer B,
1-(5,6,7,8-tetrahydro-2-naphthylacetyl)-2-(1-dimethylaminoethyl) piperidine—Diastereoisomer A,
1-(5,6,7,8-tetrahydro-2-naphthylacetyl)-2-(1-dimethylaminoethyl) piperidine—Diastereoisomer B,
1-(3,4-dichlorophenylacetyl)-2-(1-methylpyrrolidin-2-yl) piperidine—Diastereoisomer A,
1-(3,4-dichlorophenylacetyl)-2-(1-methylpiperidin-2-yl) piperidine—Diastereoisomer A, and
1-(3,4-dichlorophenylacetyl)-2-(1-methylpiperidin-2-yl) piperidine—Diastereoisomer B, 19. The method according to claim 14, wherein said haloalkyl is —$CF_3$ and said haloalkoxy is —$OCF_3$, —$OCHF_2$, —$OCF_2CF_2H$ or —$OCCl_2CF_3$.

* * * * *